United States Patent [19]

Quadro

[11] Patent Number: 4,874,776
[45] Date of Patent: Oct. 17, 1989

[54] COMPOUND HAVING MUCUS REGULATING AND ELASTASE-INHIBITORY ACTIVITIES, FOR THE THERAPY OF PULMONAL EMPHYSEMA AND PULMONAL FIBROSIS

[75] Inventor: Giuseppe Quadro, Milan, Italy

[73] Assignee: Yason S.r.l., Milan, Italy

[21] Appl. No.: 217,384

[22] Filed: Jul. 11, 1988

[51] Int. Cl.$^4$ .................. C07D 277/06; A06K 31/425
[52] U.S. Cl. ..................................... 514/365; 548/201
[58] Field of Search .......................... 548/201; 514/365

[56] References Cited

U.S. PATENT DOCUMENTS 4,374,249 2/1983 Moran ................................. 548/201

FOREIGN PATENT DOCUMENTS 115091 1/1983 European Pat. Off. ............ 514/365

OTHER PUBLICATIONS

Nakagawa, Tet. Letters, 6087 (1986).

*Primary Examiner*—Robert Gerstl
*Attorney, Agent, or Firm*—Bucknam and Archer

[57] ABSTRACT

N-carbethoxy-4-thiazolidine-carboxylic acid of formula I

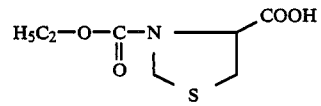

and the alkali, alkali-earth of basic amino acid salts thereof have therapeutic activities in the affections of respiratory system.

4 Claims, No Drawings

COMPOUND HAVING MUCUS REGULATING AND ELASTASE-INHIBITORY ACTIVITIES, FOR THE THERAPY OF PULMONAL EMPHYSEMA AND PULMONAL FIBROSIS

The present invention relates to a novel 4-thiazolidine-carboxylic acid derivative, namely N-carbethoxy-4-thiazolidine-carboxylic acid of formula I

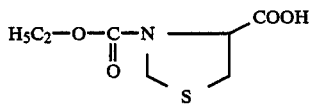 I and to the pharmaceutically acceptable acids thereof, particularly those with alkali and alkali-earth metals or those with basic amino acids, such as lysine, arginine or ornithine.

Compound of formula I, which will also be named hereinafter YS 795, has been found to have valuable therapeutic characteristics which make it useful in the treatment of both chronic and acute affections of the respiratory system, such as emphysema, pulmonal fibrosys and in all those pathological conditions characterized by an increase or impairment of secretion. Moreover, the compound of the invention has hepatoprotective activity.

Compound I is prepared by reacting a 4-thiazolidine-carboxylic acid and ethyl chlorocarbonate, in the presence of alkali bicarbonates or other bases, in anhydrous aprotic solvents, for example acetone.

The reaction is preferably carried out at temperatures from room temperature to the reflux temperature of the solvent. The salts are then obtained by means of conventional methods, such as precipitation or lyophilization.

The following example further illustrates the invention, without limiting the scope and spirit thereof.

EXAMPLE 11 g of potassium bicarbonate and 13 g of ethyl chlorocarbonate were added to a solution of 13.3 g of 4-thiazolidine-carboxylic acid in 100 ml of acetone.

The reaction mixture was refluxed for 2 hours, then left to stand overnight. A compound which could be crystallized from a 50:50 diethyl ether:petroleum ether mixture was obtained.

The compound melted at 84°–87° C.; it was unsoluble in water and soluble in common organic solvents.

Elemental analysis for $C_7H_{11}NO_4S$ (M.W.=205,142): calculated % C=40,97; H=5,40; N=6,82 found % C=41,03; H=5,43; N=6,73.

The structure of the compound was confirmed by the spectroscopic data.

I.R. spectrum (registered in nujol mull; the values of absorption bands are expressed in $cm^{-1}$: stretch O—H, broad 3600–3300, stretch C=O, acid 1740, stretch C=O, urethane 1670.

$H^1$ N.M.R. spectrum (registered in $CDCl_3$; inner standard TMS; the values of chemical shifts of the protons are in δ); 1,2 (t, 3H, $\underline{CH_3}$—$CH_2$ O); 3,3 (d, 2H, —S—$CH_2$—CH); 4–4,7 (m, 5H, $CH_3$—$\underline{CH_2}$—O; N—$\underline{CH_2}$—S; $CH_2$—$\underline{CH}$—COOH); 4,9 (s, 1H, $\overline{OH}$ mobile).

The following pharmaco-toxicological tests have been carried out on the obtained compound.

(1) Acute toxicity

Acute toxicity of YS 795 was calculated in the rat and the mouse after both oral and intraperitoneal administrations.

$LD_{50}$ was determined according to the method of Litchfield and Wilcoxon (J. Pharmacol. Exp. Therap. 96, 99–118, 1949).

The obtained results are reported in the following Table 1:

| Animal | Administration route | $DL_{50}$ mg/kg Male | Female |
|---|---|---|---|
| Rat | os | >4.000 | >4.000 |
|  | i.p. | 415 | 420 |
| Mouse | os | >4.000 | >4.000 |
|  | i.p. | 380 | 372 |

(2) Elastase-inhibitory activity

Inhibition of elastase activity by YS 795 was evaluated according to the method by D. A. Hall, S. El Ridi (Methods of connective tissue research, Ioyson-Bruvvers Ltd.; Oxford—1976) and by R. M. Senior et al. (Elastine and elastic Tissue, Plenum Press, pp. 249–254, New York—1977).

YS 795 proved to have an high elastase inhibitory activity, with a $IC_{50}$ of 11 mM.

(3) Antiemphysema activity

Emphysema induced by porcine pancreatic elastase in the hamster.

Capability of YS 795 in preventing emphysema caused by instillation of elastase was studied according to the method by Stone P. J. et al. (Am. Rev. Respir. Dis.; 124/1; 1981) and by Yu et al. ("Elastin and elastic tissues"; Plenum Press; New York; 1977).

Materials and methods

16 Hamsters weighing 100–120 g were divided in 4 groups of 4 animals each (Groups A, B, C and controls) and treated as follows:

Group A: in tratracheal instillation of 0,1 mg of porcine pancreatic elastase 1 hour after administration of 100 mg/kg of YS 795.

Group B: YS 795 was administered 1 hour after elastase instillation.

Group C: YS 795 was administered 4 hours after elastase instillation.

Controls: physiological saline was administered 1 hour after elastase instillation.

At set times (72 hours and 12 days), the animals were killed after intraperitoneal anesthesia with pentobarbital. Lungs were intubated through trachea and fixed.

Morphological and morphometrical analysis of the pulmonal sections were then carried out under a microscope.

The obtained results clearly show that YS 795 can antagonize pulmonal emphysema induced by porcine pancreatic elastase.

Said effect was found to be more marked when YS 795 was administered before elastase instillation.

(4) Collagenase inhibitory activity

The inhibition of collagenase by means of YS 795 was evaluated according to the method by C. L. Hu, G. Crombie, C. Franzeblau (Analyt., Biochem. 88, 638, 1978).

YS 795 proved to have a high elastase inhibitory activity, having a $IC_50$ of 15 mM.

(5) Bronchosecretagogue activity

Bronchosecretagogue activity was evaluated by means of sodium fluoresceine test, according to the procedure by Mawatari ("Experimental studies on the expectorant action of several drugs" Kagoshima Kaigaken Igaken Zasshi 27, 561, 1976), said test consisting in determining the sodium fluoresceine amount eliminated from respiratory tract: the higher the secretion, the higher the amount of sodium fluoresceine eliminated. Accordingly, any compound increasing the secretion of respiratory tract causes an increase in sodium fluoresceine elimination, which can easily be calculated.

Male Wistar rats (100-200 g body weight), fasted for 18 hours, with water "ad libitum", were administered with YS 795 at the dose of 100 mg/kg and, by comparison, with carboxymethyl cystein at equiponderal doses, by the oral route.

30 minutes after the treatment, sodium fluoresceine was injected subcutaneously and 30 minutes after the animals were killed by bleeding. The whole respiratory tree was then withdrawn and the percentage of sodium fluoresceine present was evaluated. The results are reported in the following Table 2.

One hour after the treatment the animals were killed by beheading; blood was collected in heparinized test-tubes and centrifuged for 10 minutes at 3500 rpm to prepare plasma. The tissues (liver, lung, kidney and brain) were homogenized in 4 volumes of 0,05M phosphate buffer.

Tissular concentrations were studied by gas-chromatographic analysis.

The obtained results show that, under the described conditions:

(1) YS 795, as such, is well adsorbed by both oral and intraperitonel route, and it is subsequently metabolized to n-thiazolidine-carboxylic acid. Plasmatic concentration peak is attained between the first and the second hour after the administration. YS 795 is still found as such till the $12^{th}$ hour.

(2) YS 795 is present in all the examined tissues, where it is found both as such and as thiazolidine-carboxylic derivative.

(3) From the verification of the concentrations in the organs, it can be desumed that YS 795 structure acts as a carrier with a marked tropism towards liver and lungs,

TABLE 2

| | BRONCHOSECRETAGOGUE ACTIVITY IN THE RAT | | | | |
|---|---|---|---|---|---|
| TREATMENT | DOSES mg/kg i.p. | N° ANIMALS | ANIMALS WEIGHT g | SODIUM FLUORESCEINE | |
| | | | | μg/ml | % Δ vs. controls |
| CONTROL | — | 10 | 99,0 ±5,56 | 0,31 ±0,02 | — |
| S—CARBOXYMETHYLCYSTEIN | 100 | 10 | 95,0 ±7,41 | 0,56 ±0,05 | 80,6 |
| YS 795 | 100 | 10 | 101,0 ±2,91 | 0,53 ±0,06 | 70,9 |

(6) Hepato-protecting activity

Hepato-protecting activity of YS 795 was evaluated in comparison with N-acetylcystein, by means of the test of hepatic intoxication induced by carbon tetrachloride, according to the method by Sanna et al. (Experientia, 32 (1), 91, 1976).

Male Wistar rats (268-346 g body weight) fasted for 18 hours, with water "ad libitum", were used.

YS 795 and N-acetylcystein were administered intraperitoneally at the dose of 100 mg/kg, whereas the control group received the only carrier.

15 minutes after the drug administration, the animals were treated orally with 0,15 ml/kg of carbon tetrachloride.

After 24 more hours, the animals were killed by bleeding after ether anesthesia.

The results are reported in the following Table 3.

in which the drug amounts were found to be remarkanly higher after treatment with YS 795 in comparison with thiazolidine-carboxylic acid.

(8) Clinical studies

YS 795 in capsules was administered to hospitalized patients affected by chronic bronchitis, in order to test tolerability and mucus regulating activity.

10 patients, 5 males and 5 females, of 65-70 years age, smokers or ex-smokers, were treated with YS 795 administered at a dose of 3×300 mg capsules a day, in the morning, at noon and in the night, with full stomach, for a period of 4 weeks.

All drugs having mucolytic, bronchodynamic, steroidal and balsamic activities were excluded during the observation period, whereas the "routine" therapy of concomitant diseases, based on administration of diuretic, hypotensive, antidiabetic, vasodilating and anti-

TABLE 3

| | HEPATO-PROTECTING ACTIVITY | | | | |
|---|---|---|---|---|---|
| TREATMENT | DOSES mg/kg i.p. | CODE | WEIGHT (g) x ± es | GPT U/L x ± es | % INHIBITION VS. CONTROLS |
| CONTROL | — | A | 286,8 ± 7,89 | 357,0 ± 117,48 | — |
| N—ACETYLCYSTEIN | 100 | C | 306,8 ± 5,92 | 168,2 ± 8,68 | 52,9 |
| YS 795 | 100 | G | 309,2 ± 9,37 | 220 ± 84,47 | 38,4 |

(7) Pharmacokinetics

Male CD-COBS rats weighing 200-220 g were used, treated with YS 795 and 4-thiazolidine-carboxylic acid by the oral or intraperitoneal route, in equimolecular amounts (YS 795=795=100 mg/kg; thiazolidine-carboxylic acid =65 mg/kg).

biotic drugs, was continued.

Before and after the treatment, tests were carried out to evaluate possible side-effects of YS 795 on hemopoietic, hepatic and renal functions; heart rate and arterial pressure were further checked during the treatment.

At the end of the 4 week treatment, the following results were observed:

YS 795 at the dose of 3 capsules/day turned out to be well tolerated at gastric level;

the laboratory tests carried out before and after the treatment, show that YS 795 does not affect hemopoietic, hepatic and renal functions;

no clinically significant effects on arterial pressure and heart rate were evidenced;

the lack in side-effects allows to suggest the use of YS 795 for prolonged treatments;

YS 795 proved to have good fluidifying and mucus regulating activities, positively interfering on the impaired secretion synthesis which is generally observed in all the cases of respiratory tract phlogosis.

From what stated above, the compound of the invention clearly turns out to be useful in therapy.

The present invention also relates to all the industrially applicable aspects related to therapeutical use of YS 795.

Thus, a main object of the invention is provided by pharmaceutical compositions containing predetermined and effective amounts of YS 795, suited for oral, rectal, parenteral on inhalatory administrations of the compounds of the invention.

Examples of said pharmaceutical compositions are capsules, sugar-coated pills, tablets, syrups, suppositories, vials or ampoules for injection, aerosols, possible sustained release forms, obtained for example by microincapsulation. The daily dose can range from 200 mg to 2 g of the active ingredient or the equivalent of the salts thereof, in one or more administrations.

I claim:

1. N-carbethoxy-4-thiazolidine-carboxylic acid lysine salt.

2. The method of treatment of chronic and acute affections of the respiratory system and hepatic intoxication which consists of administering to a subject in need of such treatment a compound which is a N-carbethoxy-4-thiazolidine-carboxylic acid of formula I

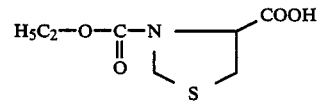

in the amount of 200–2 g daily or a pharmaceutically acceptable salt thereof which is an alkali, an alkaline earth, a basic amino acid salt in an equivalent amount.

3. A pharmaceutical composition having mucus regulating, antiemphysema, antielastase and hepatroprotecting activities, containg as the active ingredient a therapeutically effective amount of a compound which is a N-carbethoxy-4-thiazolidine-carboxylic acid of formula I

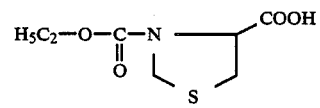

or a pharmaceutically acceptable salt thereof, selected from the group consisting of alkalai, alkaline-earth or basic amino acid salts and a carrier.

4. The composition according to claim 3 in form of capsules, sugar-coated pills, tablets, syrups, suppositories or solutions.

* * * * *